(12) United States Patent
Brodaczewski et al.

(10) Patent No.: US 10,660,650 B2
(45) Date of Patent: May 26, 2020

(54) RETAINER FOR POLYMERIC LIGATING CLIP CARTRIDGE

(71) Applicants: Wieslaw Mieczyslaw Brodaczewski, Brentford (GB); Andrzej Janusz Decewicz, Nottingham (GB)

(72) Inventors: Wieslaw Mieczyslaw Brodaczewski, Brentford (GB); Andrzej Janusz Decewicz, Nottingham (GB)

(73) Assignee: GRENA USA LLC, Wilmington, DE (US)

( * ) Notice: Subject to any disclaimer, the term of this patent is extended or adjusted under 35 U.S.C. 154(b) by 205 days.

(21) Appl. No.: 16/021,332

(22) Filed: Jun. 28, 2018

(65) Prior Publication Data

US 2019/0008521 A1  Jan. 10, 2019

Related U.S. Application Data

(60) Provisional application No. 62/529,734, filed on Jul. 7, 2017.

(51) Int. Cl.
*A61B 17/122* (2006.01)

(52) U.S. Cl.
CPC ........ *A61B 17/1222* (2013.01); *A61B 17/122* (2013.01)

(58) Field of Classification Search
USPC .................................................. 206/338, 339
See application file for complete search history.

(56) References Cited

U.S. PATENT DOCUMENTS

| 4,361,229 | A | * | 11/1982 | Mericle | A61B 17/128 |
| | | | | | 206/339 |
| 4,834,096 | A | | 5/1989 | McKinney | |
| 4,936,447 | A | * | 6/1990 | Peiffer | A61B 17/1222 |
| | | | | | 206/339 |
| 4,972,949 | A | * | 11/1990 | Peiffer | A61B 17/1222 |
| | | | | | 206/339 |
| 5,062,846 | A | | 11/1991 | McKinney | |
| 5,100,416 | A | | 3/1992 | McKinney | |
| 6,419,682 | B1 | * | 7/2002 | Appleby | A61B 17/1222 |
| | | | | | 206/339 |
| 6,880,699 | B2 | | 4/2005 | Gallagher | |
| 8,042,687 | B2 | * | 10/2011 | Cannady | A61B 17/1222 |
| | | | | | 206/339 |
| 2009/0152147 | A1 | * | 6/2009 | Cannady | A61B 17/1222 |
| | | | | | 206/339 |
| 2017/0311954 | A1 | | 11/2017 | Brodaczewski | |

* cited by examiner

*Primary Examiner* — Jacob K Ackun
(74) *Attorney, Agent, or Firm* — Seth Natter; Natter & Natter

(57) ABSTRACT

A retainer for a ligating clip cartridge includes a peripheral skirt nested within the cartridge. The retainer includes a planar peripheral top margin surface extending from the skirt. A plurality of spaced rectilinear upwardly arched boundary leaves project from opposite sides of the top margin surface. The distal ends of the boundary leaves include a pair of spaced, downwardly inclined integral distensions. When positioned within a cartridge loaded with clips, the distensions are registered with and spaced above bosses which extend transversely from each clip leg. Should the clips tend to prolapse within the cartridge; the bosses engage a keeper notch formed at the juncture between the upwardly arched boundary leaves and the downwardly inclined distensions to maintain the clips in position suitable for dispensing.

20 Claims, 8 Drawing Sheets

RETAINER FOR POLYMERIC LIGATING CLIP CARTRIDGE

RELATED APPLICATIONS

This application claims the benefit of Provisional Application No. 62/529,734, filed Jul. 7, 2017, the entirety of which is incorporated herein by reference.

BACKGROUND OF THE INVENTION

1. Field of the Invention

This invention relates generally to the storage of polymeric ligating clips in a clip cartridge and more specifically to an improved retainer for preventing clips from prolapsing during transport and handling of the cartridge.

2. Antecedents of the Invention

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel.

Ligation of vessels or other tissues have been performed by closing the vessel with a ligating clip, or by suturing the vessel with surgical thread. The use of surgical thread for ligation required complex manipulations of the needle and suture material to form the knots required to secure the vessel. Such complex manipulations were time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs. At some point thereafter, the clip is removed by using a separate instrument dedicated for that purpose, i.e., a clip removal instrument.

Asymmetric polymeric clips have been disclosed in Patent Application Publication US 2017/0311954 A1, U.S. Pat. Nos. 4,834,096 and 5,062,846 which are incorporated herein by reference.

These plastic clips generally comprise a pair of curved legs joined at their proximal ends with an integral hinge or heel. The distal ends of the curved legs include interlocking latching members. For example, the distal end of one leg terminates in a lip or hook structure into which the distal end of the other leg securely fits to lock the clip in place. The distal ends of each leg also include a pair of lateral bosses that are engaged by the jaws of a clip applier. A clip applier specifically designed for asymmetric plastic clips is used to close the clip around the tissue to be ligated, and to latch or lock the clip in the closed condition. In operation, the jaws of the clip applier are actuated into compressing contact with the legs of the clip. This causes the legs to pivot inwardly about the hinge, thereby deflecting the hook of the one leg to allow reception therein of the distal end of the other leg. A clip applier designed for use with asymmetric plastic clips in an open (i.e., non-endoscopic) surgical procedure is disclosed in U.S. Pat. No. 5,100,416, incorporated herein by reference.

Because the asymmetric plastic clips are small and several clips are often used in a surgical procedure, holding devices are employed to store and retain the clips between the time of their manufacture and packaging and ultimate use in a surgical procedure. Numerous clip cartridges have been developed, some of which strived to prevent the clips from becoming unduly loosened or even completely dislodged during shipment and handling, an example of which is disclosed in U.S. Pat. No. 6,880,699 which is incorporated herein by reference.

SUMMARY OF THE INVENTION

An improved clip retainer for a compartmentalized polymeric ligating clip cartridge includes a peripheral skirt configured to be nested within the cartridge. The retainer includes a planar peripheral top margin surface extending from the skirt. A plurality of spaced rectilinear upwardly inclined boundary leaves project from opposite sides of the top margin surface. The distal ends of the boundary leaves include a pair of spaced, downwardly inclined integral distensions.

When positioned within a cartridge loaded with clips, the distensions are registered with and spaced above bosses which extend transversely from each clip leg. If the clips tend to prolapse during shipment or handling, but limited slippage is permitted until the bosses engage a keeper notch formed at the juncture between the upwardly inclined boundary leaves and the downwardly inclined distensions to maintain the clips in position suitable for dispensing.

From the foregoing compendium, it will be appreciated that an aspect of the present invention is to provide a retainer for a polymeric ligating clip cartridge of the general character described which is not subject to the aforementioned disadvantages of the antecedents of the invention.

A feature of the present invention is to provide a retainer for a polymeric ligating clip cartridge of the general character described which is simple to use.

A consideration of the present invention is to provide a retainer for a polymeric ligating clip cartridge of the general character described which assures that clips will be retained in their respective cartridge compartments for engagement by a clip applying instrument.

Another aspect of the present invention is to provide a retainer for a polymeric ligating clip cartridge of the general character described which may be installed in a loaded clip cartridge without difficulty.

A further feature of the present invention is to provide a retainer for a polymeric ligating clip cartridge of the general character described which is well suited for economical mass production fabrication.

An additional consideration of the present invention is to provide a retainer for a polymeric ligating clip cartridge of the general character described which assures that clips carried in the cartridge are ready for use.

To provide a retainer for a polymeric ligating clip cartridge of the general character described downwardly inclined distensions are registered with bosses of polymeric ligating clip to securely restrain the clips against prolapse.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown.

DESCRIPTION OF THE INVENTION

Figure 1:
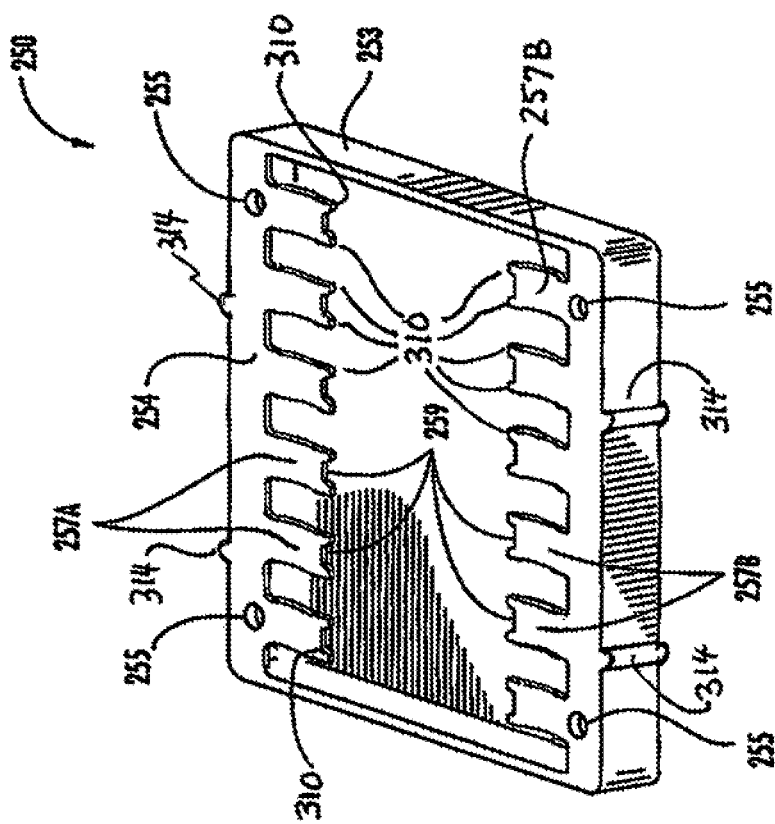
FIG. 1 is an isometric view of an improved clip retainer in accordance with the present invention and showing upwardly inclined boundary leaves projecting from opposite sides of a top margin surface.
Figure 2:
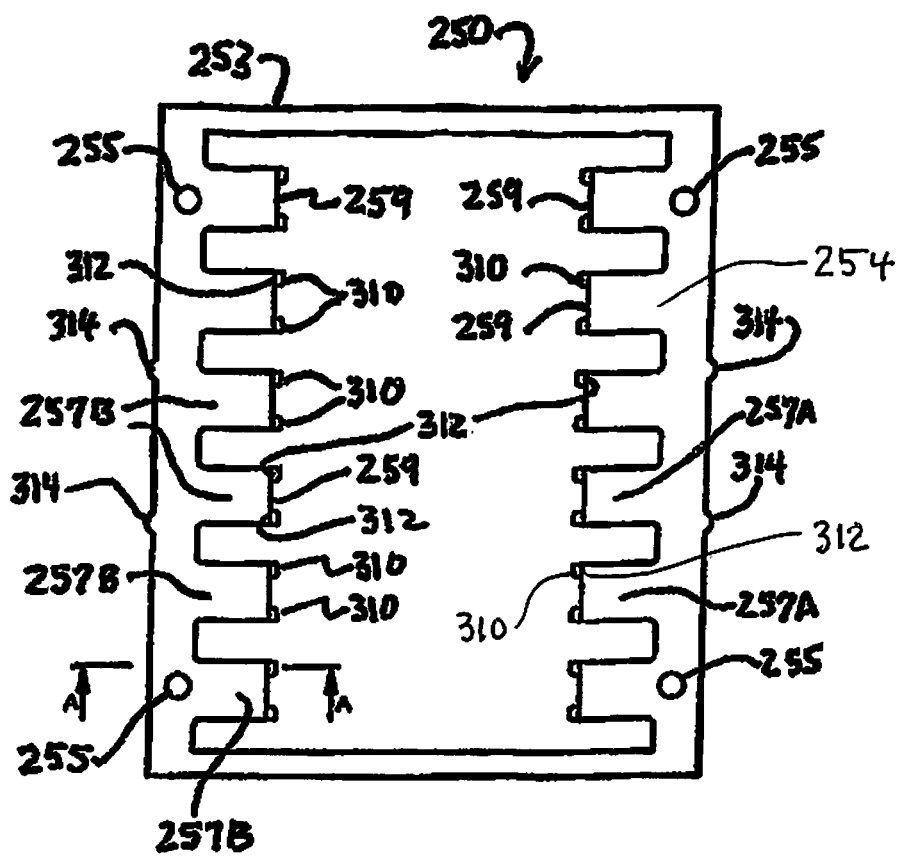
FIG. 2 is a top plan view of the clip retainer.
Figure 3:
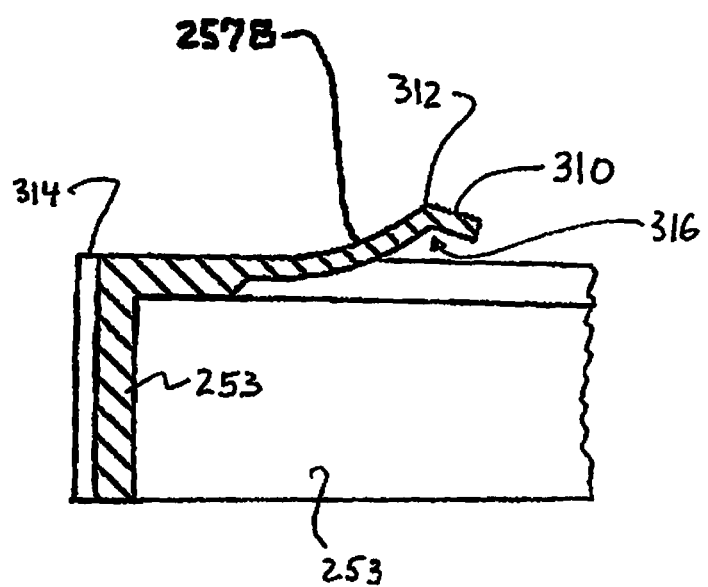
FIG. 3 is an enlarged scale fragmentary sectional view of the clip retainer, the same taken along the plane A-A of FIG. 2 and through an upwardly arched boundary leaf with a downwardly inclined distal distension.
Figure 4:
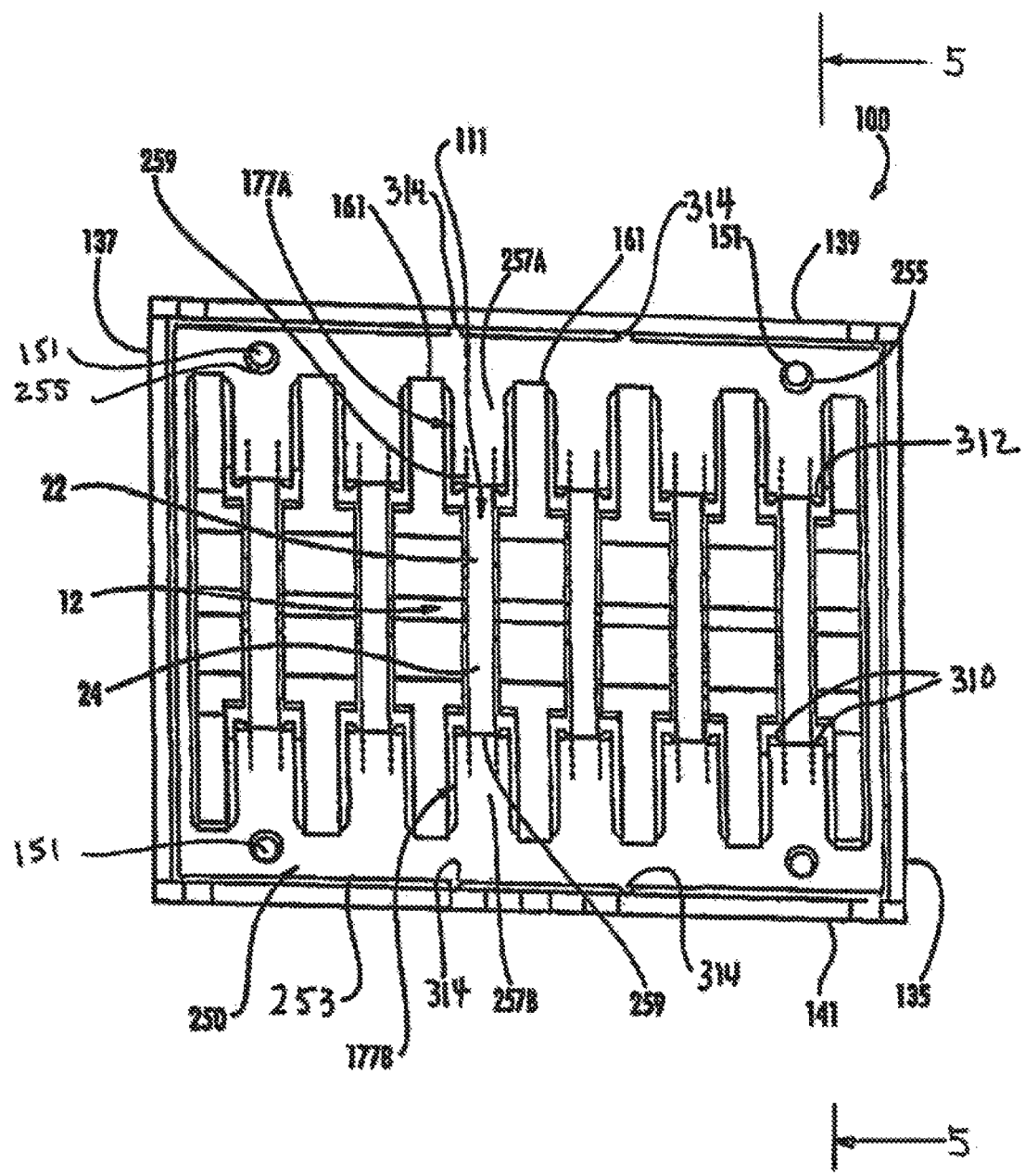
FIG. 4 is a plan view of an assembled cartridge loaded with clips and secured with the clip retainer of the present invention.
Figure 5:
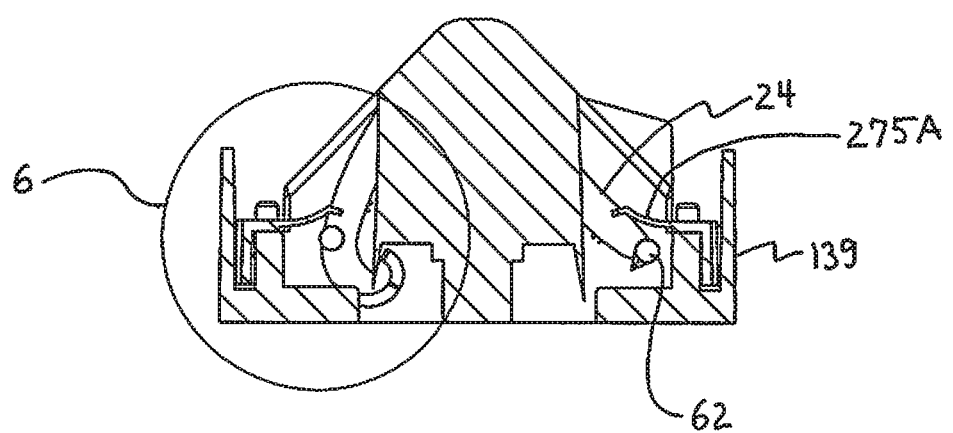
FIG. 5 is an enlarged scale cross sectional view through the assembled cartridge taken substantially along the plane 5-5 of FIG. 4 and showing a clip in an originally placed normal position.
Figure 5A:
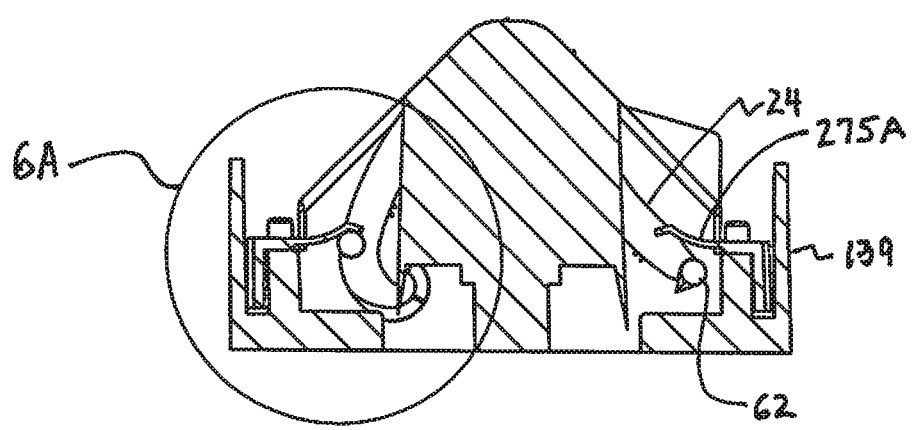
FIG. 5A is a cross sectional view through the assembled cartridge, similar to FIG. 5, but showing the clip having slipped from its normal storage position yet being restrained from prolapsing out of a dispensable position by the clip retainer in accordance with the invention.

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein by way of illustration.

This invention relates to an improved clip retainer suitable for implementation with the cartridge disclosed in U.S. Pat. No. 6,880,699 which is incorporated herein in its entirety by reference. For continuity, the component numeral designations of U.S. Pat. No. 6,880,699 will be employed herein to denote the same or corresponding structure described and shown therein.

An improved clip retainer 250 for a compartmentalized polymeric ligating clip cartridge 100 includes a peripheral skirt 253 configured to be nested within the cartridge 100. The retainer 250 is preferably constructed from a resilient material such as translucent or transparent polyethylene and includes a planar peripheral top margin surface 254 extending from the skirt 253.

An aperture 255 through the top margin surface 254 adjacent each corner thereof receives a locating post 151 which extends from an inner side wall 145 of a cartridge base 131 adjacent each corner thereof, as described and illustrated in U.S. Pat. No. 6,880,699.

In accordance with the present invention, a plurality of axially spaced pairs of rectilinear upwardly arched boundary leaves 257A, 257B, project inwardly toward each other from opposite sides of the top margin surface 254. The distal ends of the boundary leaves 257A, 257B, include a central cut away depression 259 which defines a pair of integral distensions 310. The integral distensions are downwardly inclined from the boundary leaves 257A, 257B at a crease line 312, which is coincident with the central cut away depression 259.

Figure 6:
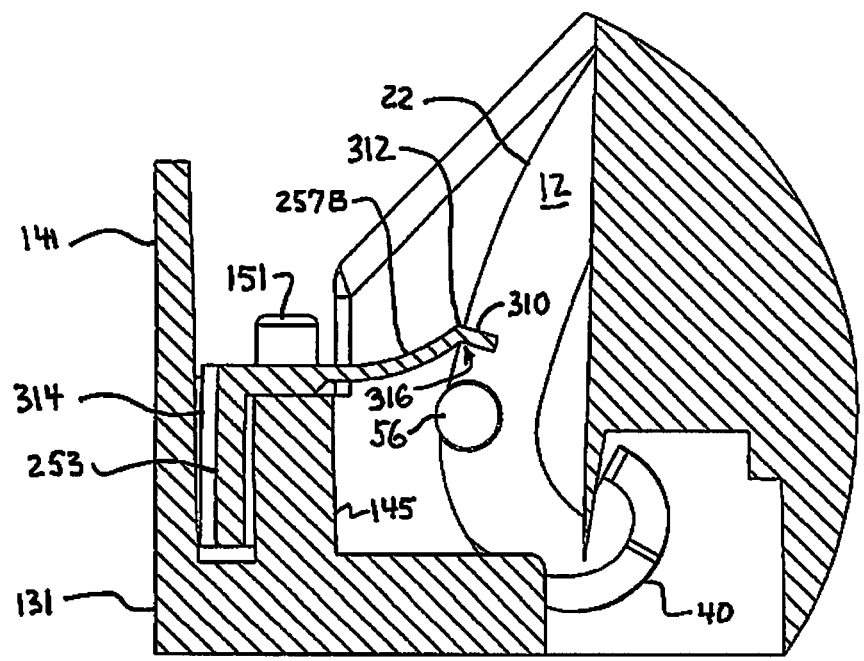
FIG. 6 is a view of the circled portion 6, of FIG. 5, which has been enlarged for magnification.
Figure 6A:
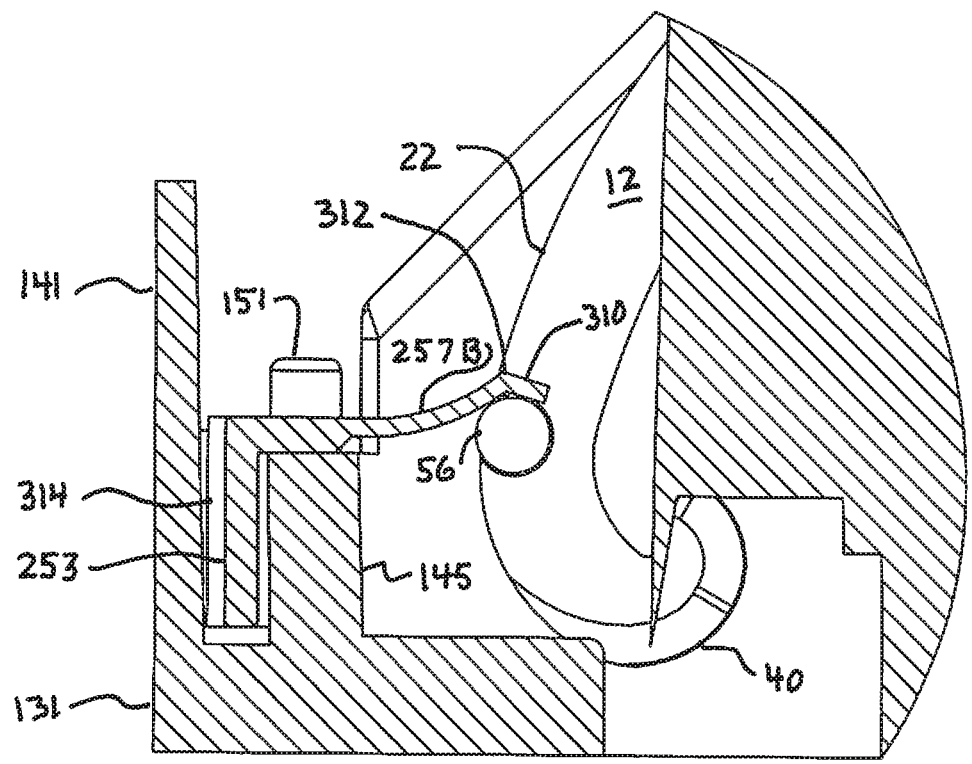
FIG. 6A is a view of the circled portion 6A, of FIG. 5A, which has been enlarged for magnification.

When positioned within a cartridge 100 loaded with clips 12, the distensions 310 are spaced above bosses 56, 62, which extend transversely from each clip leg 22, 24. If the clips 12 tend to prolapse during shipment or handling, but limited slippage is permitted until the bosses 56, 62, engage a keeper notch 316 formed on the underside of the clip retainer 250 at the junction between the boundary leaves 257A, 257B and the downwardly inclined distensions 310, as illustrated in FIG. 6A The clips 12 are thus maintained the in position suitable for easy removal by an applicator instrument.

To further assure that the clips will not be dislodged from their respective compartments, two opposed walls of the peripheral outer frame skirt 253 include projecting ribs 314 which tightly engage the inner face of the base side walls 139, 141. Thus, the clip retainer 250 is secured in the base 131; the clips 12 will not prolapse out of the cartridge 100 and the clip retainer 250 will not deflect as a result of forces applied due to the tendency of the clips to open.

Thus it will be seen that there is provided a retainer for a polymeric ligating clip cartridge which achieves the various aspects, features and considerations of the present invention and which is well suited to meet the conditions of practical usage.

In the figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element or step, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention as claimed. It is felt therefore that these embodiments should not be limited to the disclosed embodiment but rather should be limited only by the spirit and scope of the appended claims.

Having thus described the invention, there is claimed as new and desired to be secured by Letters Patent:

1. A retainer for a ligating clip cartridge comprising a plurality of spaced rectilinear leaves projecting from a generally planar surface, the leaves including an upwardly inclined portion and at least one downwardly inclined integral distension, a keeper notch formed at the juncture between the upwardly inclined portion and the downwardly inclined distension, the retainer being dimensioned such that the keeper notch will engage a ligating clip within the cartridge to preclude prolapsing during shipment and handling of the cartridge.

2. The retainer for a ligating dip cartridge as constructed in accordance with claim 1 wherein the distal ends of the leaves comprise a pair of spaced integral distensions dimensioned to engage bosses which project transversely from a leg of the clips to preclude the clips from prolapsing.

3. The retainer for a ligating clip cartridge as constructed in accordance with claim 1 wherein the generally planar surface comprises a peripheral top margin and the leaves project from opposite sides of the peripheral top margin.

4. The retainer for a ligating dip cartridge as constructed in accordance with claim 3 wherein the retainer further includes a peripheral skirt extending downwardly from the top margin, the peripheral skirt being configured to nest within the cartridge.

5. The retainer for a ligating dip cartridge as constructed in accordance with claim 4 further including ribs projecting from opposed walls of the peripheral skirt, the ribs tightly engaging opposed inner faces of the cartridge.

6. The retainer for a ligating clip cartridge as constructed in accordance with claim 1 wherein the upwardly inclined portion is arched.

7. The retainer for a ligating clip cartridge as constructed in accordance with claim 1 wherein the distal end of each leaf includes a cut away portion which defines a pair of spaced integral distensions.

8. The retainer for a ligating clip cartridge as constructed in accordance with claim 4 the peripheral top margin including a plurality of apertures, the apertures being dimensioned to receive locating posts which project from the cartridge when the peripheral skirt is nested within the cartridge.

9. The retainer for a ligating clip cartridge as constructed in accordance with claim 1 wherein the leaves are rectilinear.

10. A method of precluding ligating clips stored in a compartmentalized cartridge from prolapsing during shipment and handling, the method comprising the steps of:
    a) providing a retainer as constructed in accordance with claim 4,
    b) registering the leaves with the clips stored in each compartment,
    c) nesting the peripheral skirt within the cartridge, and
    d) employing the keeper notch to restrain clip movement.

11. A retainer for a ligating clip cartridge the retainer comprising a generally planar peripheral top margin, a plurality of spaced rectilinear leaves projecting from opposite sides of the peripheral top margin, each leaf including an upwardly ached portion and at least one downwardly inclined portion, a keeper notch formed at the juncture the upwardly arched portion and the downwardly inclined portion, the retainer being dimensioned such that the keeper notch will engage a clip positioned within the cartridge to preclude the dip from prolapsing during shipment and handling of the cartridge.

12. The retainer for a ligating dip cartridge as constructed in accordance with claim 11 wherein the distal ends of the leaves include a cut away which extends into the downwardly inclined portion from the distal end of each leaf toward the keeper notch.

13. The retainer for a ligating dip cartridge as constructed in accordance with claim 12 wherein the cut away defines pair of spaced integral distensions dimensioned to engage bosses which project transversely from legs of the clips.

14. The retainer for a ligating clip cartridge as constructed in accordance with claim 11 the retainer further including a peripheral skirt extending downwardly from the peripheral top margin, the peripheral skirt being configured to nest within the cartridge.

15. A method of precluding ligating clips stored in a compartmentalized cartridge form prolapsing during shipment and handling, the method comprising the steps of:
    a) providing a retainer as constructed in accordance with claim 13,
    b) nesting the peripheral skirt within the cartridge, and
    c) employing the keeper notch to restrain clip movement.

16. A compartmentalized ligating clip cartridge carrying a plurality of ligating clips, the cartridge comprising a base having a plurality of compartments, the ligating clips being received in the compartments, the cartridge including a pair of opposed side walls and a pair of axial end walls, the compartments bring defined by a plurality of transverse walls, the cartridge further including a ligating clip retainer, the ligating clip retainer comprising a generally planar peripheral surface, a plurality of spaced leaves projecting from the peripheral surface, each leaf being registered with and overlying a ligating clip received within a compartment, each leaf including a keeper notch, the retainer being dimensioned such that the keeper notch will engage a ligating dip to preclude the ligating dip from prolapsing during shipment and handling of the cartridge.

17. The compartmentalized ligating clip cartridge as constructed in accordance with claim 16 wherein each leaf is comprised of two portions, the keeper notch being formed at the juncture of the two portions.

18. The compartmentalized ligating clip cartridge as constructed in accordance with claim 17 wherein the two portions comprise an upwardly ached portion extending proximally from the peripheral surface and a downwardly inclined portion spaced from the peripheral surface.

19. The compartmentalized ligating clip cartridge as constructed in accordance with claim 18 wherein the downwardly inclined portion includes a cut away which extends into the downwardly inclined portion from the distal end of each leaf toward the keeper notch.

20. The compartmentalized ligating clip cartridge as constructed in accordance with claim 18 wherein each ligating clip includes a pair of legs joined at one end by a hinge, at least one leg having a pair of bosses adjacent the end of the at least one leg spaced from the hinge, the bosses projecting transversely from opposite sides of the at least one leg, the cut away defining the downwardly inclined portion into a pair of spaced integral distensions dimensioned to engage the bosses.

* * * * *